US011021356B2

(12) United States Patent
Naaber

(10) Patent No.: US 11,021,356 B2
(45) Date of Patent: Jun. 1, 2021

(54) BOTTLE CLOSING DEVICE FOR PLACING PRESS-FIT CLOSURES, SUCH AS CROWN CORKS, CROWN CAPS, AND SIMILAR CLOSURES, ON BOTTLES OR SIMILAR CONTAINERS

(71) Applicant: Matthias Naaber, Bretzenheim (DE)

(72) Inventor: Matthias Naaber, Bretzenheim (DE)

(73) Assignee: KHS GMBH, Dortmund (DE)

( * ) Notice: Subject to any disclaimer, the term of this patent is extended or adjusted under 35 U.S.C. 154(b) by 461 days.

(21) Appl. No.: 15/481,522

(22) Filed: Apr. 7, 2017

(65) Prior Publication Data
US 2017/0297882 A1  Oct. 19, 2017

Related U.S. Application Data

(63) Continuation-in-part of application No. PCT/EP2015/072527, filed on Sep. 30, 2015.

(30) Foreign Application Priority Data

Oct. 7, 2014 (DE) ............ 10 2014 114 561.5

(51) Int. Cl.
*A61L 2/18* (2006.01)
*A61L 2/20* (2006.01)
(Continued)

(52) U.S. Cl.
CPC ............ *B67B 3/10* (2013.01); *A61L 2/18* (2013.01); *A61L 2/20* (2013.01); *B67B 3/12* (2013.01); *A61L 2202/17* (2013.01)

(58) Field of Classification Search
CPC .. B67B 3/12; B67B 3/2066; B67C 2007/0066
(Continued)

(56) References Cited

U.S. PATENT DOCUMENTS 4,527,377 A * 7/1985 Hayashi ............ B67B 3/00
141/90
5,040,354 A * 8/1991 Ahlers ............ B67B 3/00
53/167
(Continued)

FOREIGN PATENT DOCUMENTS

DE   39 18 504         12/1990
DE   41 10 456 A1       3/1992
(Continued)

*Primary Examiner* — Thanh K Truong
*Assistant Examiner* — Patrick B Fry
(74) *Attorney, Agent, or Firm* — Nils H. Ljungman & Associates

(57) ABSTRACT

A bottle closing device for placing press-fit closures, such as crown corks, crown caps, and similar closures, on bottles or similar containers. The abstract of the disclosure is submitted herewith as required by 37 C.F.R. § 1.72(b). As stated in 37 C.F.R. § 1.72(b): A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims. Therefore, any statements made relating to the abstract are not intended to limit the claims in any manner and should not be interpreted as limiting the claims in any manner.

14 Claims, 14 Drawing Sheets

(51) Int. Cl.
*B67B 3/10* (2006.01)
*B67B 3/12* (2006.01)

(58) Field of Classification Search
USPC .......................... 53/342, 329, 331.5; 141/92
See application file for complete search history.

(56) References Cited

U.S. PATENT DOCUMENTS

| | | | | |
|---|---|---|---|---|
| 5,842,322 | A * | 12/1998 | Heudecker | B67B 3/10 53/319 |
| 6,945,011 | B2 * | 9/2005 | Hidding | B67B 3/00 53/167 |
| 7,661,245 | B2 * | 2/2010 | Brown | B67B 3/2066 53/317 |

FOREIGN PATENT DOCUMENTS

| | | |
|---|---|---|
| DE | 43 32 740 A1 | 3/1995 |
| DE | 196 26 680 A1 | 1/1998 |
| GB | 770 745 A | 3/1957 |

* cited by examiner

BOTTLE CLOSING DEVICE FOR PLACING PRESS-FIT CLOSURES, SUCH AS CROWN CORKS, CROWN CAPS, AND SIMILAR CLOSURES, ON BOTTLES OR SIMILAR CONTAINERS

CONTINUING APPLICATION DATA

This application is a Continuation-In-Part application of International Patent Application No. PCT/EP2015/072527, filed on Sep. 30, 2015, which claims priority from Federal Republic of Germany Patent Application No. 10 2014 114 561.5, filed on Oct. 7, 2014. International Patent Application No. PCT/EP2015/072527 was pending as of the filing date of this application. The United States was an elected state in International Patent Application No. PCT/EP2015/072527.

BACKGROUND

1. Technical Field

The present application relates to a bottle closing device for placing press-fit closures, such as crown corks, crown caps, and similar closures, on bottles or similar containers.

2. Background Information

Background information is for informational purposes only and does not necessarily admit that subsequently mentioned information and publications are prior art.

Closing tools and closing machines are used for closing bottles or similar containers, wherein press-fit closures, such as crown corks, crown caps, and similar closures, are placed over the mouths of the bottles. The closing of bottles with such press-fit closures can involve first placing the closure onto the mouth of a bottle. A closing punch, drawing tool, or similar closing arrangement is then moved toward the bottle, often by lowering, so as to engage a die ring, drawing ring, or closing die with a portion of the closure. The die ring then deforms the portion of the closure to press fit the closure onto the bottle. One of the most common types of press-fit closures is a crown cap, also known as a crown cork. Crown caps generally have a flat, circular, inner portion that is designed to cover the mouth opening in a bottle, and a ring-shaped or annular outer edge portion that includes a number of teeth. To install a crown cap on a bottle, the inner portion of the crown cap is positioned over the mouth of the container. The closing punch is lowered to cause the die ring to engage the outer edge portion of the crown cap. The die ring then deforms or bends the outer edge portion with respect to the inner portion. The die ring is pressed into the outer edge portion of the crown cap until the outer edge portion is bent around and crimped onto the mouth portion of the bottle, usually below or behind a beading or protruding lip at the mouth of the bottle. After completing the deformation step, the closing punch is then moved or raised away from the bottle. The teeth on the outer portion of the crown cap are now crimped onto the mouth of the bottle to firmly hold the crown cap in place and resist accidental opening. In such a closing device, the die ring can be arranged in a die ring receptacle or support body of the closing punch or a die ring holder formed from this.

Since the closing device is used to close bottles or similar containers filled with a product, there is a need to keep the closing device clean. Dirt and other environmental contaminants can build up on the parts and surfaces of the closing device, which contaminants could possibly be accidentally transferred into the product in the bottles. Microorganisms, such as bacteria, and other organic contaminants could also build up on the closing device. Further, there is a good chance that some of the product itself could be accidentally deposited onto parts of the closing device, which could lead to the build up of contaminants. One possible solution or technique to address such contamination is to have the closing device or components thereof periodically treated with a treatment material. For example, the closing device could be cleaned and/or disinfected from time to time, i.e. at specified or preselected intervals of time, using a cleaning and/or disinfection medium. The cleaning and/or disinfecting process, such as, for example, a cleaning-in-place (CIP) cleaning and/or disinfection procedure, could be performed by treatment or flushing of the closing device component(s) with a liquid and/or gaseous and/or vaporous cleaning and/or disinfection medium. Such a cleaning and/or disinfecting process should be focused on treating the surface(s) of the component(s) of the closing device that come in contact with the closures, and thus are most likely to transfer contaminants to the closures and/or the product in the container. For example, the closing punch, especially the die ring, should be specifically treated since they are either in contact with or in close proximity to the closure during closing of the bottle. Unfortunately, due to the design of the components of the closing device, such treatment procedures are essentially only possible on exposed surfaces of the components. Consequently, any unexposed or concealed surfaces of the components of the closing device may possibly be untreated and thus may have contaminants thereon.

OBJECT OR OBJECTS

An object of the present application is to provide a closing tool or closing device which allows for improved cleaning and/or disinfection in relation to other closing tools or closing devices, specifically in the region of the die ring holder and the die ring.

SUMMARY

To achieve this object, a closing tool is configured in accordance with the present application. A die ring for use with the closing tool is also an object of the present application.

The present application is based on the recognition that, to promote optimum cleaning and/or disinfection of the closing tool, it may be necessary and/or desired not only for the exposed surfaces to be treated with the cleaning and/or disinfection medium, but also the unexposed surfaces of the closing tool. To further explain, the die rings that are used to contact and deform the press-fit closures, according to one possible exemplification, may be seated in a die ring receptacle, which could be an opening formed in a support body that is recessed or stepped or tapered. The die ring receptacle can essentially or substantially match the dimensions of the die ring so that the die ring fits snugly or in a relatively flush manner in the die ring receptacle. As a result of this snug fit, the surfaces of the die ring receptacle, such as, for example, the surfaces of axial and radial supporting regions, as well as the surfaces of the die ring in contact against or facing these supporting regions, are essentially unexposed. Despite the snug fit, there can still be a small gap or a transition or a space between the facing surfaces of the die ring receptacle and the die ring. Contaminants can intrude into this gap and build up therein. The problem is that while the gap is wide enough to permit the entry of contaminants, it is sufficiently small to prevent or restrict the entry of a treatment medium, and thus prevent or restrict treatment and/or removal of the contaminants.

According to one exemplification of the present application, the closing tool has a high degree of operational reliability, i.e. with reliable anchoring of the die ring to the die ring holder. In a further exemplification of the present application, the closing tool is configured, for example, such that:

the flow paths are in each case configured as continuous or substantially continuous between an underside and an upper side of the die ring holder and the die ring, and, related for example to the tool axis, extend at least axially or essentially axially, in one possible exemplification also radially or essentially radially, and/or tangentially or essentially tangentially, or that the die ring receptacle, or the opening forming this receptacle, is profiled on its inner surface, and/or the die ring is profiled on the circumferential and/or face surface supporting the die ring holder, and possibly in each case for the formation of a plurality of raised regions and indentations or troughs, adjacent to these raised regions, and, for example, at least partially surrounding them, and that the raised regions in their totality form the contact surface of the die ring receptacle and/or the contact surface of the die ring, or that the surface dimension of the totality of the contact or support surfaces for the die ring, formed from the raised regions, is perceptibly smaller than the surface dimension which non-profiled contact or support surfaces for the die ring would comprise in totality, for example by at least fifty percent, or that the profiling is configured in the form of grooves and webs lying between them, forming the contact or support surfaces, or that the profiling is configured for the support of the die ring, axially relative to the tool axis, by a plurality of projections, which are spaced at a distance from one another and are provided distributed about the tool axis or the axis of the die ring, in the opening and/or on a face surface of the die ring, or that the grooves forming the profiling are configured with their longitudinal extension parallel or essentially parallel to the tool axis or to an axis of the die ring or obliquely or in helical form relative to these axes, or that additional grooves or indentations are provided in the webs, which in each case open at both ends into a groove separating two webs, and are oriented, for example relative to the machine axis or relative to the axis of the die ring, tangentially or essentially tangentially, or that the projections serving to provide the axial support for the die ring are formed in each case at a web, and in one possible exemplification transfer into a common projection, which is formed annular in shape, and, surrounding the tool axis, extends into the die ring receptacle or into the opening forming this receptacle, or that the die ring is arranged floating, i.e. with a certain axial and/or radial play, in the die ring receptacle or opening of the die ring holder, or that in the die ring holder, at least one channel is provided, opening into the gap between the die ring holder and adjacent surfaces of the die ring, for delivering and removing the treatment medium, wherein the at least one channel is open, in one possible exemplification on a surface of the die ring holder outside the die ring receptacle or the opening forming this receptacle, or that the at least one channel opens into at least one groove, formed in the die ring receptacle or opening, and surrounding the tool axis, for example at least partially, or that two grooves are provided, offset to one another axially relative to the tool axis, into which in each case at least one channel opens, and which are connected to one another with regard to flow movement, or that the webs laterally adjacent to the at least one groove form the axial and radial supporting regions of the die ring, and that this supporting region in one possible exemplification comprises the profiling, wherein the foregoing features can be present in each case individually or in any desired combination.

According to at least one possible exemplification, the bottle closing device comprises a pressing arrangement and a moving arrangement that moves the pressing arrangement back and forth. In one possible exemplification, the moving arrangement moves the pressing arrangement up and down. The pressing arrangement includes a head portion that engages a press-fit closure, such as a crown cap. The head portion can be made up of two parts: a die ring for deforming the closure, and a support body to carry the die ring. The support body has an opening therein in which the die ring is seated or supported.

Continuous or substantially continuous flow passages are formed between facing surfaces of the die ring holder and the die ring. These passages can be oriented to extend at least axially or essentially axially, and/or radially or essentially radially, and/or tangentially or essentially tangentially, with respect to a longitudinal axis or tool axis of the closing tool.

In one possible exemplification, at least one of the surfaces of the opening in the support body is profiled, and/or the die ring is profiled on its circumferential and/or face surface. In each case, the profiling results in the formation of a plurality of alternating raised regions and indentations or troughs. The raised regions can together form the contact surface of the opening with respect to the die ring, or the contact surface of the die ring with respect to the opening.

The expression "essentially" or "approximately" or "approx" in the meaning of the present application signifies deviations from the respective exact value by +/−10%, in one possible exemplification by +/−5%, and/or deviations in the form of changes which are not of significance to the function.

Further exemplifications, advantages, and possible applications of the present application are also derived from the following description of exemplifications and from the figures. In this context, the features described or pictorially represented are in principle the object of the present application, individually or in any desired combination, regardless of their relationship in the claims or reference to them. The contents of the claims are also constituent parts of the description.

The above-discussed exemplifications of the present invention will be described further herein below. When the word "invention" or "exemplification of the invention" is used in this specification, the word "invention" or "exemplification of the invention" includes "inventions" or "exemplifications of the invention", that is the plural of "invention" or "exemplification of the invention". By stating "invention" or "exemplification of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

DESCRIPTION OF EXEMPLIFICATION OR EXEMPLIFICATIONS

Figure 1:
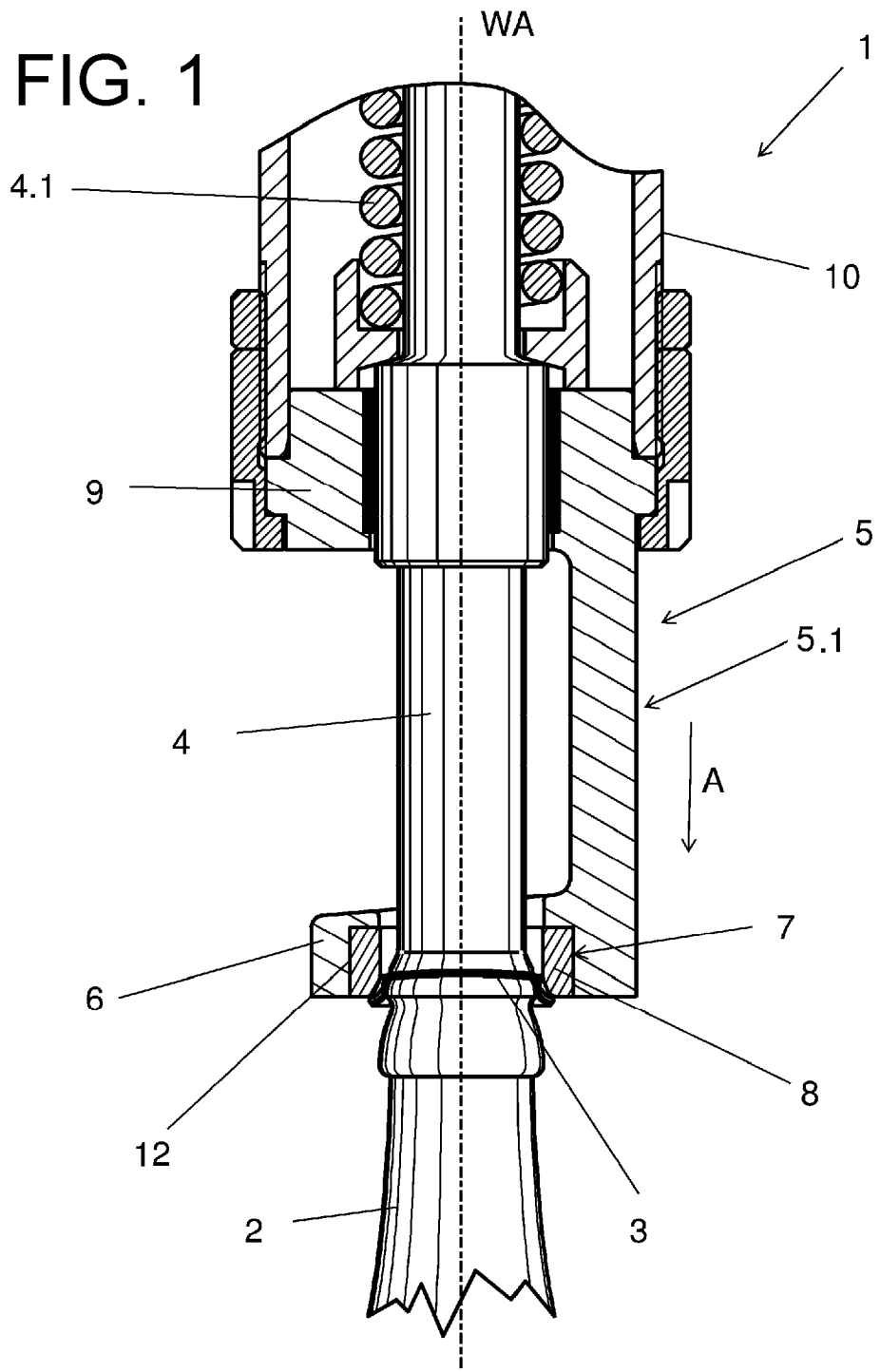
FIG. 1, in a partial representation and in section, shows a closing tool for the closing of containers in the form of bottles with crown cork closures.

The closing tool 1, as shown in general in FIG. 1, serves to close containers in the form of bottles 2 with crown caps or crown corks 3, and is a component part of a corresponding closing machine. The closing machine could be, for example, a closing machine of the circulating or rotary type that includes a plurality of closing tools 1 positioned about the circumference of a rotor driven to rotates about a vertical machine axis. Corresponding to the representation in FIG. 1, the closing tool 1 comprises, among other elements, a hold-down device 4, in the form of a punch, which is spring-loaded by a hold-down spring 4.1 and is arranged coaxially with a tool axis WA. In the exemplification in FIG. 1, the tool axis WA is oriented vertically. During a closing procedure, a crown cap 3 is pressed and held against the opening of the bottle 2 by the hold-down device. The closing tool 1 also comprises a closing punch or closing arrangement 5. The closing punch 5, in the exemplification in FIG. 1, has an approximately annular die ring holder 6 disposed on the lower end of the closing punch 5. The die ring holder 6 comprises an opening or recess or recessed opening 7 arranged coaxially with the axis WA, which opening 7 functions as a receptacle for a die ring 8. The die ring 8, in the exemplification represented, is configured on the underside as a ring in circular cylindrical form, with an inclined inner edge region 8.1 (see FIG. 2). The opening 7 of the die ring holder 6 forms for the die ring 8, among other things, supporting regions 7, 7.1 to support or hold the die ring 8 in place. Supporting region 7.1 is oriented to run essentially radially with respect to the axis WA, and thus provides support in an essentially axial direction for the upper surface of the die ring 8 in contact with the supporting region 7.1. Supporting region 7.2 is oriented to run essentially axially with respect to the axis WA, and thus provides support in an essentially radial direction for the circumferential surface or casing surface of the die ring 8 in contact with the supporting region 7.2.

At the upper end in FIG. 1, the closing punch 5 is configured with a connecting or holding section 9, which surrounds the closing punch 5, and with which the closing punch 5 is secured, in a replaceable manner, to a tubular housing part 10. The housing part 10, among other things, surrounds concentrically, or essentially concentrically, the hold-down element 4 and the hold-down element spring 4.1. The die ring 8 is held in the opening 7 in a suitable manner, for example by a plate 11 (FIG. 3) secured to the underside of the closing punch 5. The closing punch 5 comprises, for example, a body portion 5.1 between the die ring holder 6 and the connecting or holding section 9. The body portion 5.1 is formed in the manner of a shell that partially surrounds the hold-down element 4. The body portion 5.1 could have an arcuate or curved or substantially C-shaped or semi-circular cross-section, as shown, for example, in FIG. 3.

Hereinafter, in accordance with one exemplification, the side of the die ring holder 6 facing towards the connecting or holding section 9 is designated as the upper side, and the side facing away from the holding and connecting section 9 is designated as the underside.

When the bottle 2 concerned is being closed, the closing punch 5, with the housing part 10, moves downwards in the direction of the axis WA (arrow A) toward the crown cap 3, which is placed on the bottle 2 and pressed and held there with the hold-down element 4. To secure the crown cap 3 and close the bottle 2, the closing punch 5 is moved downward to the extent that the edge portion of the crown cap 3 is deformed by the die ring 8, and the edge region 8.1 of the die ring 8 remains or is moved behind the mouth beading of the bottle 2. After the closing, the closing punch 5 is raised again.

For such closing tools 1, a treatment of the closing tool 1 may be required and/or desired to be performed periodically at least at predetermined or preselected intervals of time. It may be particularly important to perform a treatment of the sections or surfaces of the sections of the closing tool 1 that come in direct contact with the crown caps 3, such as, for example, the die ring holder 6 and the die ring 8, with a treatment medium comprising a liquid and/or gaseous and/or vaporous cleaning and/or disinfection medium. According to the concept on which the present application is based, this treatment must or may take place not only on the directly exposed surfaces of the closing tool 1, but also on the unexposed or partially unexposed surfaces. In the situation of the die ring holder 6 and of the die ring 8, it is recognized that a possibly critical and unexposed region, which is therefore likewise to be treated, is a transition or gap 12 between the outer surface of the die ring 8 and the inner surface of the die ring holder 6 surrounding the die ring 8.

In order to allow for an intensive treatment of these surfaces which define the gap 12, the present application therefore proposes, as a departure from the prior art, that the opening 7 forming the die ring receptacle in the die ring holder 6 is profiled. Specifically, the surfaces of the die ring holder 6 about the opening 7 may be profiled, at least at the supports 7.1 and 7.2, and/or the die ring 8 itself is profiled on its circumferential surface and, for example, also on its face surface. The profiling of the surfaces of the opening 7 and/or the die ring 8 is done specifically in order to form a plurality of raised regions and, adjacent to these, for example also surrounding them, indentations or troughs. At the locations at which the opening 7 and/or the die ring 8 exhibit this profiling, the contact of the die ring 8 on the die ring holder 6 then occurs on the contact surfaces formed by the raised regions, the surface dimension of which in total is perceptibly smaller than that surface dimension which the contact surfaces would in total exhibit between the die ring holder 6 and the die ring 8 without this profiling.

Figure 2:
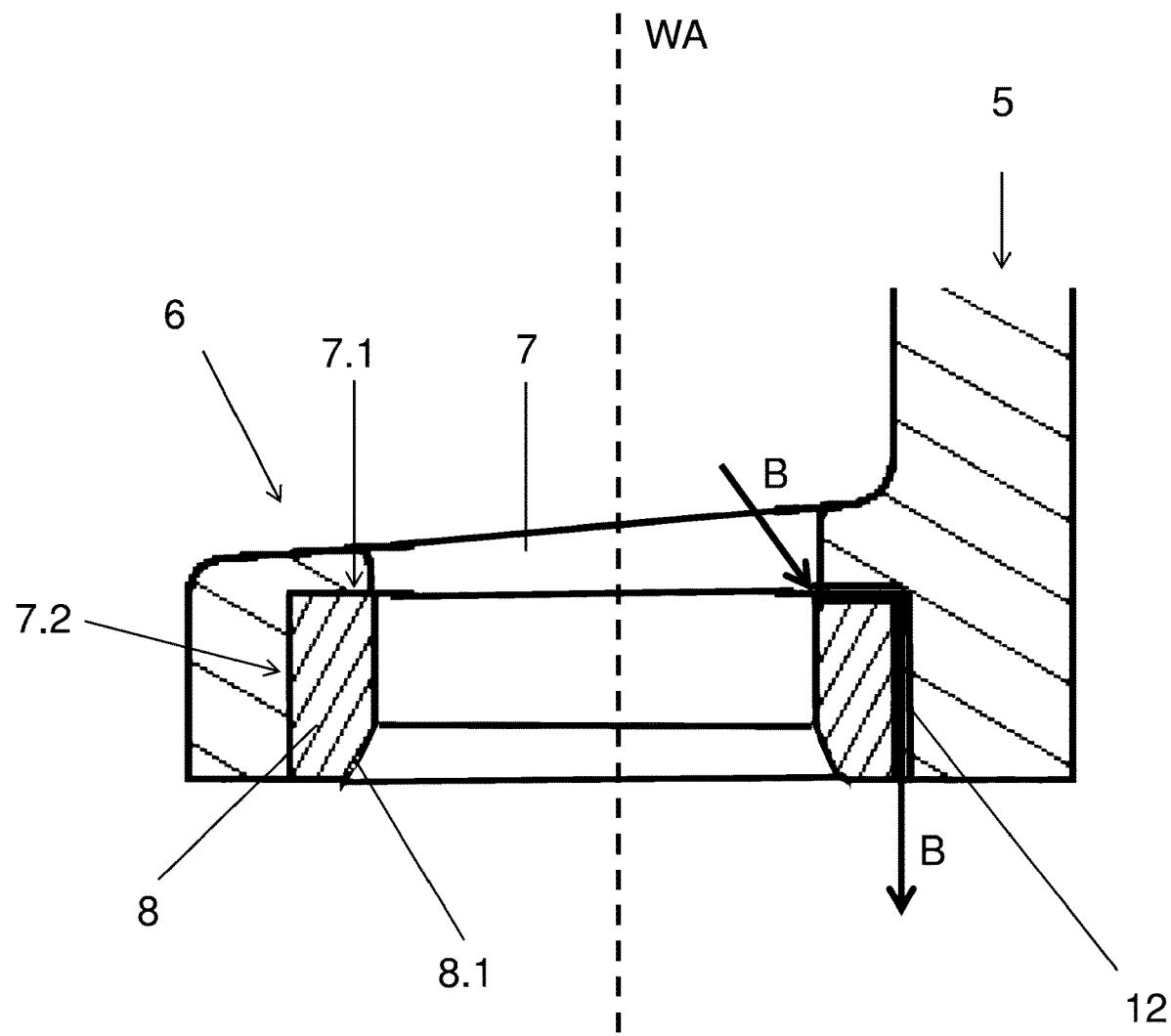
FIG. 2, in an enlarged individual representation, shows the die ring of the closing tool from FIG. 1, held in a die ring holder.

The profiling, however, is also, in one possible exemplification, configured in such a way that, in the gap 12 along the plurality of raised regions and, as appropriate, also surrounding them, a flow path or passage is formed. The liquid and/or gaseous and/or vaporous treatment medium can flow through this flow path or passage, such as between the upper side of the die ring 8 and the underside of the die ring holder 6, and between the circumferential outer surface of the die ring 8 and the annular inner surface of the die ring holder 6, as indicated in FIG. 2 by the arrows B.

Figure 3:
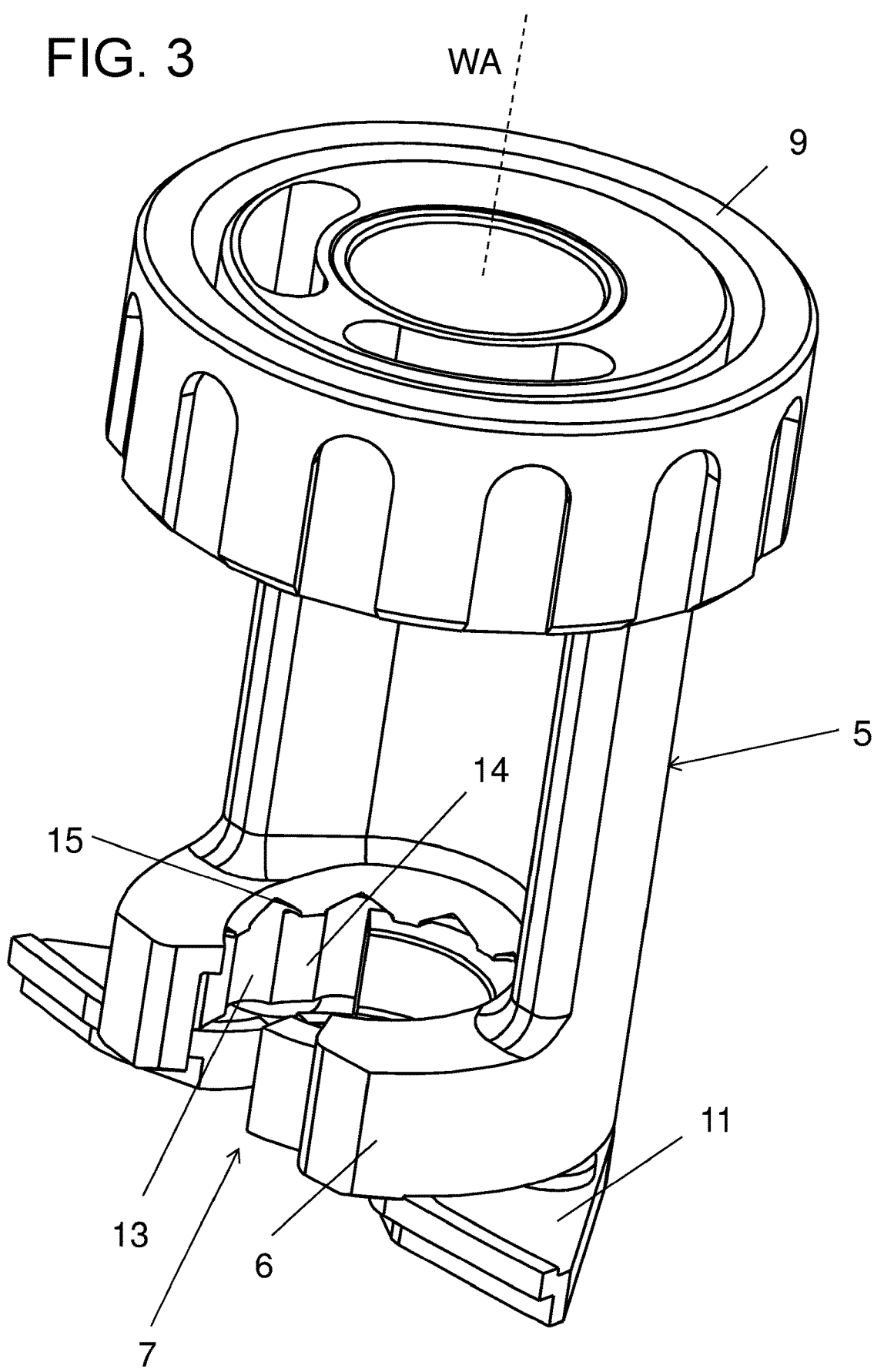
FIGS. 3-11, in each case in perspective representation, show the closing punch of the closing tool with different exemplifications of the die ring holder or, respectively, the die ring receptacle of this holder.
Figure 4:
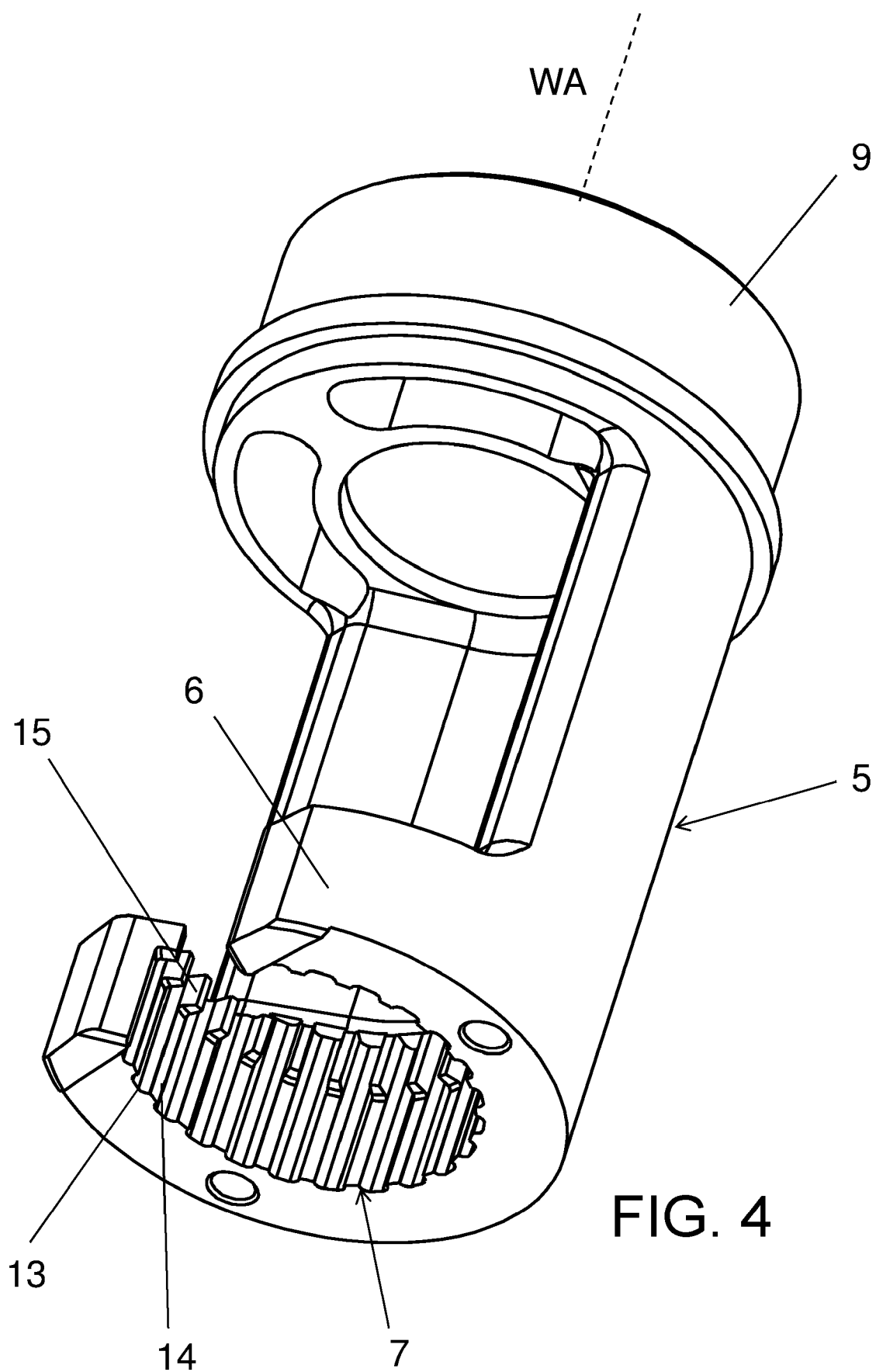

As the FIGS. 3-11 show, the profiling can be realized at the supporting regions 7.1 and 7.2 of the die ring holder 6 in several differing manners. For example, in the exemplification of the die punch 5 in FIGS. 3 and 4, the opening 7 is provided on its inner surface, which forms the radial supporting region, with a plurality of groove-shaped indentations 13, which in each case extend parallel or substantially parallel to the axis WA, and are open on the upper side and underside of the die ring holder 6. The webs 14 formed, in each case, between two grooves 13, which are arranged with their longitudinal extension likewise parallel or substantially parallel to the axis WA, exhibit in the region of their upper end, i.e. in the region of the upper side of the die ring holder 6, in each case a projection 15, projecting radially inwards into the opening 7, relative to the axis WA. The projections 15 form in their totality the axial supporting region, and the webs 14 in their totality form the radial supporting region of the opening 7. It is possible for the treatment medium to flow via the grooves 13 through the gap 12. The exemplifications represented in FIGS. 3 and 4 may differ from one another in that the axial and radial supporting regions of the opening 7 are more finely structured in the exemplification in FIG. 4 than with the exemplification in FIG. 3, i.e. the number of grooves 13, webs 14, and projections 15 with the closing punch 5 in FIG. 4 is greater than with the closing punch 5 in FIG. 3.

Figure 5:
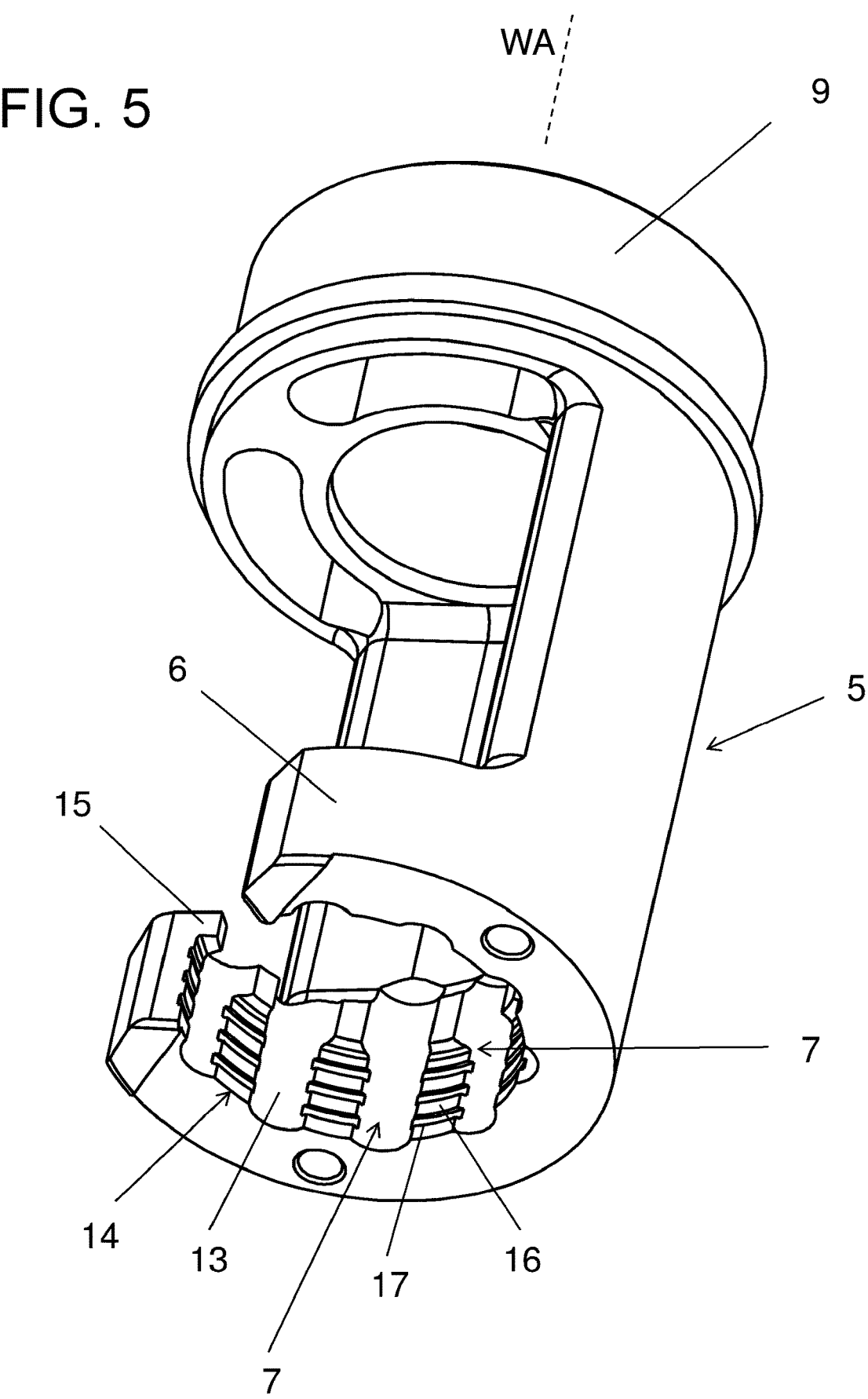

FIG. 5 shows as a further exemplification a closing punch 5, with which the supporting regions 7.1 and 7.2 of the opening 7 are structured similarly to FIGS. 3 and 4, and specifically with grooves 13 and webs 14, the latter being provided in each case on the upper side of the die ring holder 6 with a projection 15. As a departure from FIGS. 3 and 4, with the closing punch 5 in FIG. 5, however, the webs are in their turn additionally profiled, and possibly in order to form raised regions, which form the contact surfaces for the die ring 8, as well as with the formation of indentations or troughs adjacent to the raised regions. In the exemplification in FIG. 5, the webs 14 are provided for this purpose, on their surface facing towards the axis WA, with additional grooves 16, opening at both ends in each case into a groove 13. Webs 17 are formed between the additional grooves 16, which webs 17, together with the webs 14, form the total radial contact region for the die ring 8. Webs 17 extend, for example just as the grooves 16, tangentially to an imaginary circle surrounding the axis WA. By means of the additional grooves 16 and webs 17, a multiple-branched flow of the treatment medium in the gap 12 is possible, i.e. a flow which comprises a component that is axial, radial, and also tangential to the axis WA.

For the closing punches 5 shown in FIGS. 3-5, the grooves 13 and projections 15 extend as far as the upper side of the die ring holder 6, facing towards the holding section 9. In contrast, FIGS. 6-11 show exemplifications of the closing punch 5 in which the opening 7 forming the die ring receptacle, on the upper side of the die ring holder 6, tapers to a diameter which is smaller than the outer diameter of the die ring 8. To further explain, the opening designated in these figures in general by 7a, and corresponding to the opening 7, comprises, on the upper side of the die ring holder 6, a continuous annular shoulder or projection 18, surrounding the axis WA and projecting into the opening 7a.

Figure 6:
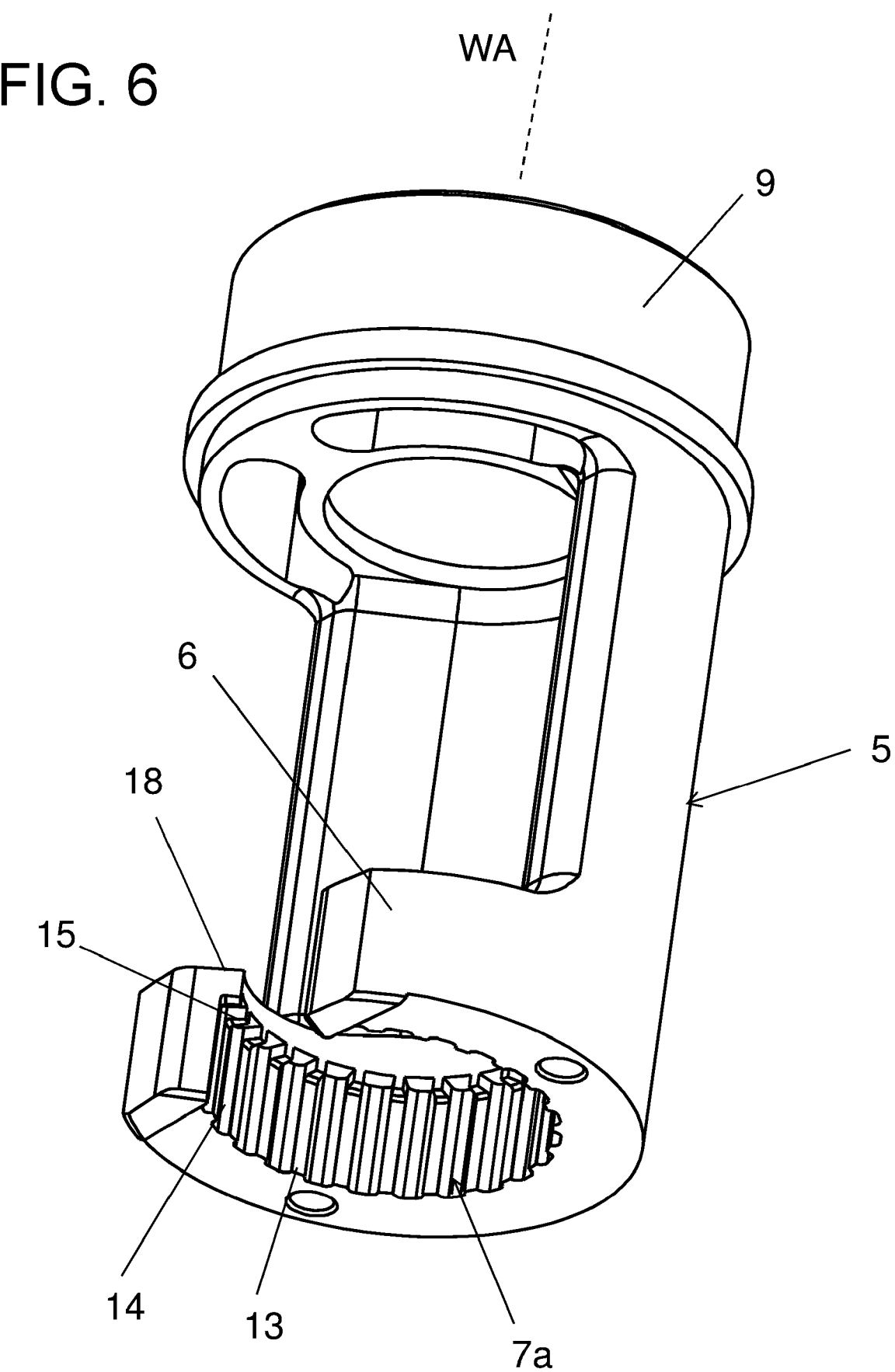

This tapering, according to one exemplification, is formed in order to increase the mechanical strength. Apart from this, the closing punch 5 in FIG. 6 is profiled at the supporting regions for the die ring 8 in a similar manner to the closing punch 5 in FIG. 4, i.e., is provided with grooves 13 and webs 14, which have at their upper end the projections 15. The grooves 13 extend from the underside of the die ring holder 6 or the opening 7 respectively as far as the projection 18. The projections 15, starting from the upper side of the die ring holder 6, connect to the projection 18, and are spaced apart from one another along the projection 18 in such a way that, in the gap 12 between the die ring 8 and the die ring holder 6, a plurality of flow channels or passages are formed, which extend between the upper side and underside of the die ring holder and are formed by the grooves 16 and the intermediate spaces between the projections 15.

Figure 7:
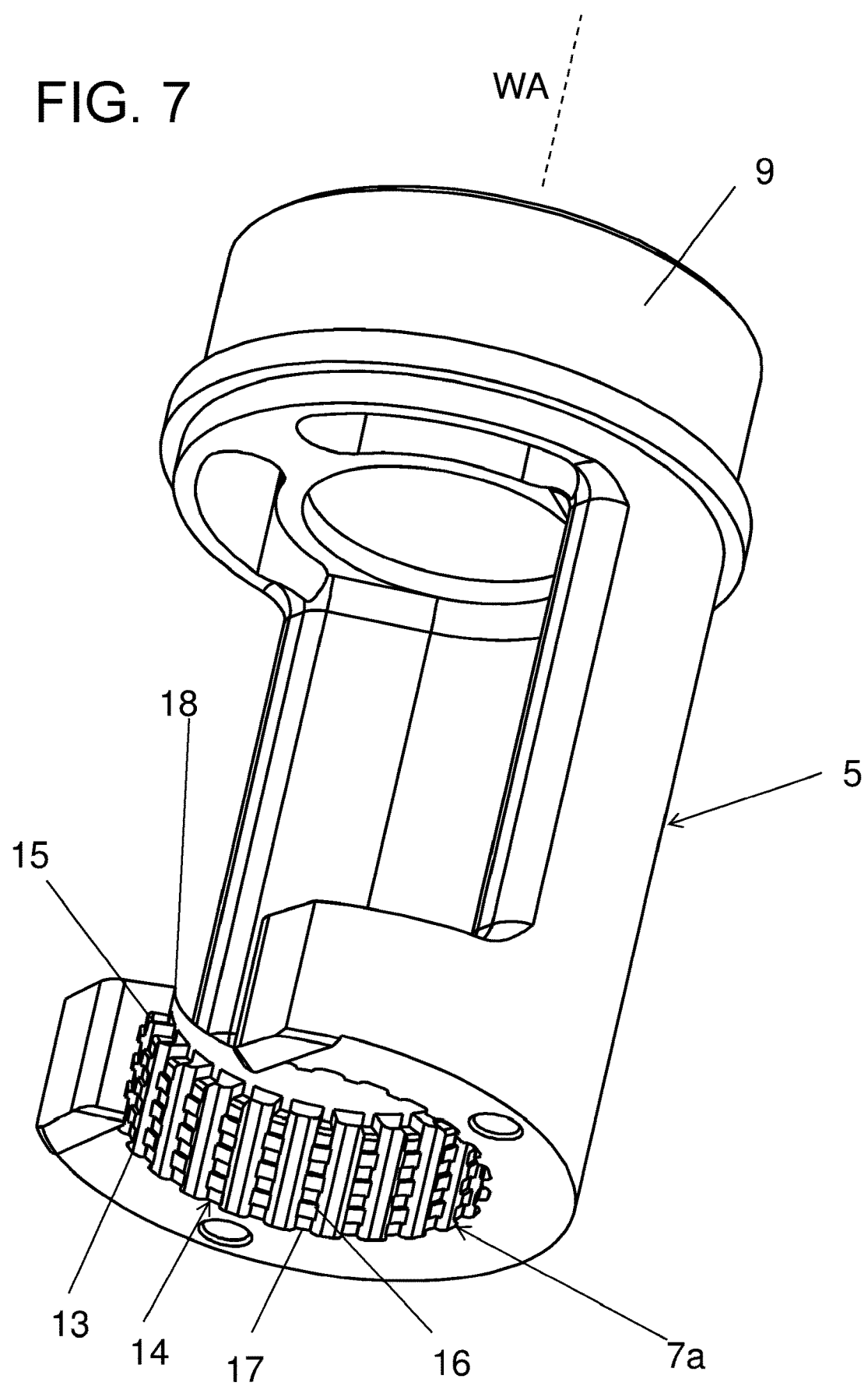

FIG. 7 shows as a further exemplification a closing punch 5, which differs from the closing punch 4 in FIG. 6 in that the webs 14 are additionally profiled, i.e. they comprise the additional grooves 16 and webs 17, which, in this exemplification, because of their short length, also appear as projections and indentations. Due to the additional grooves 16 and webs 17, a multiple-branched flow of the treatment medium in the gap 12 is possible, i.e. a flow which comprises a component that is axial, radial, and also tangential to the axis WA.

Figure 8:
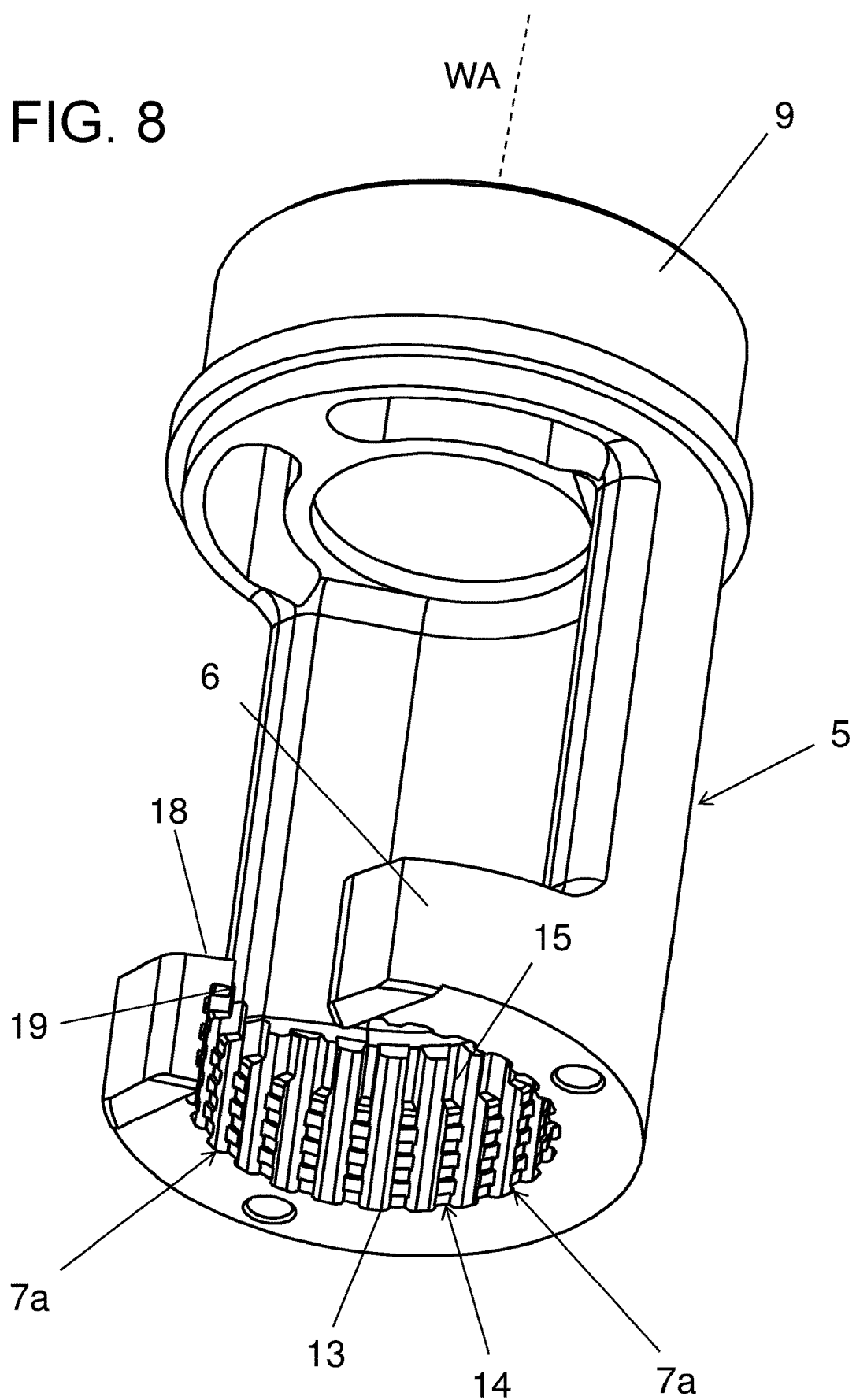

FIG. 8 shows as a further exemplification a closing punch 5, which essentially differs from the closing punch 5 in FIG. 7 in that the projections are in each case spaced apart axially from the projection 18 relative to the axis WA, such that an annular flow channel 19 is formed between the projection 18 and the projections 15, into which the grooves 16 extend and which, relative to the axis WA, is open on the inside.

Figure 9:
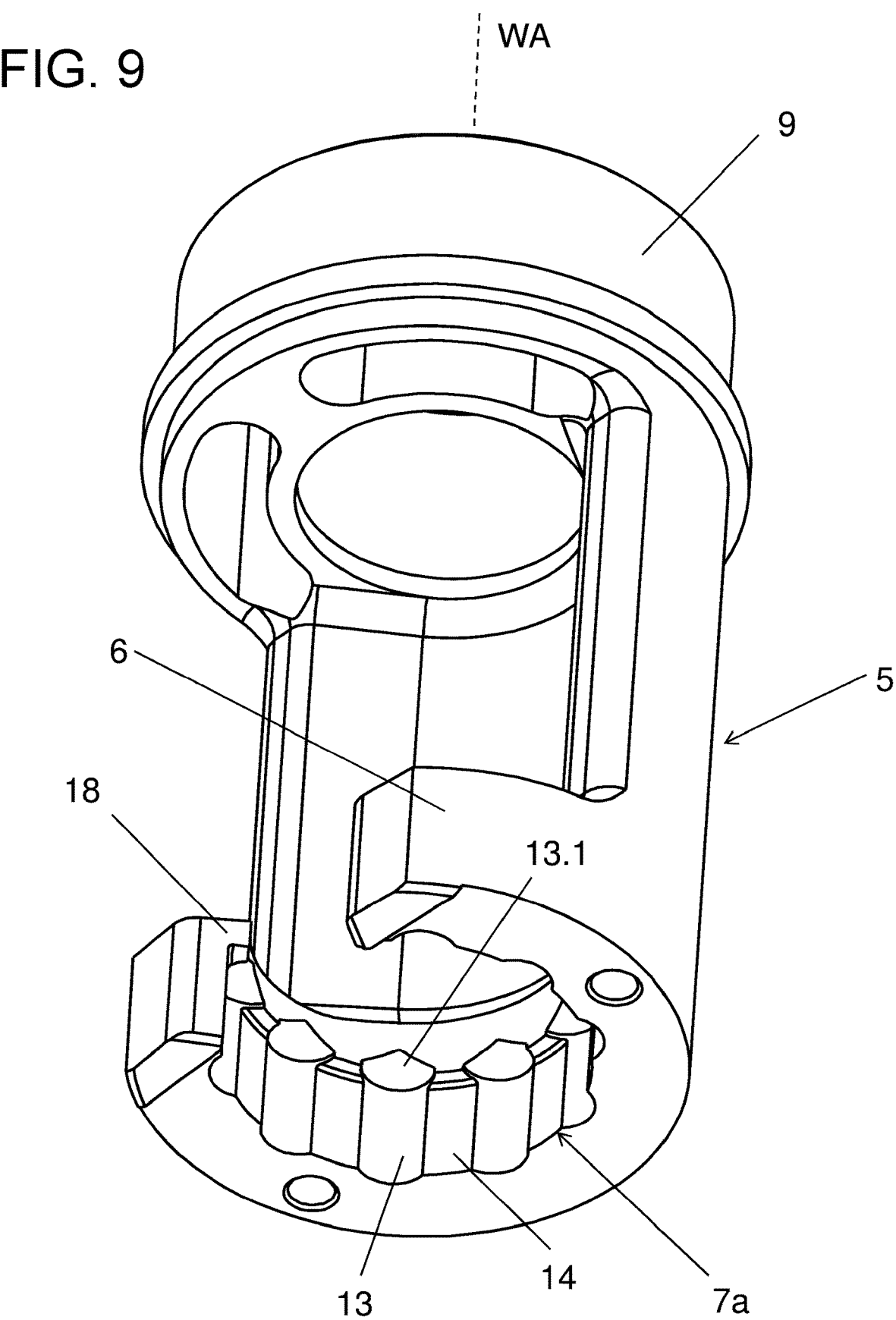

FIG. 9 shows as a further exemplification a closing punch 5, with which the projection 18 forms the axial supporting region of the opening 7a for the die ring 8, and the grooves 16, open on the underside of the die ring holder 6, extend as far as into the projection 18, and there are open at an opening 13.1 facing towards the axis WA.

Figure 10:
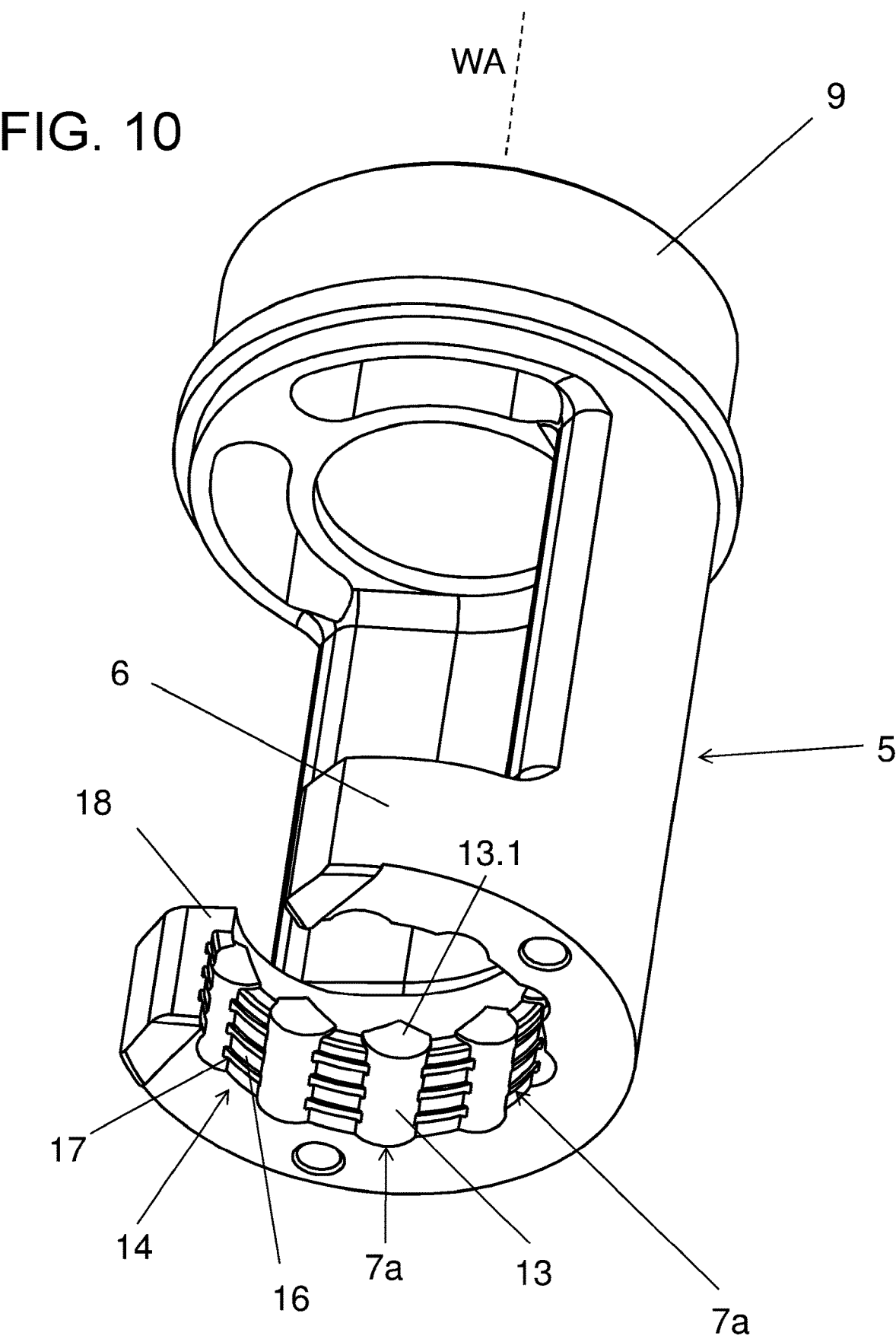

FIG. 10 shows an exemplification of the closing punch 5, which differs from the exemplification in FIG. 9 in that the webs 14 in turn comprise the additional grooves 16, opening at both ends in each case into a groove 13, and the webs 17.

Figure 11:
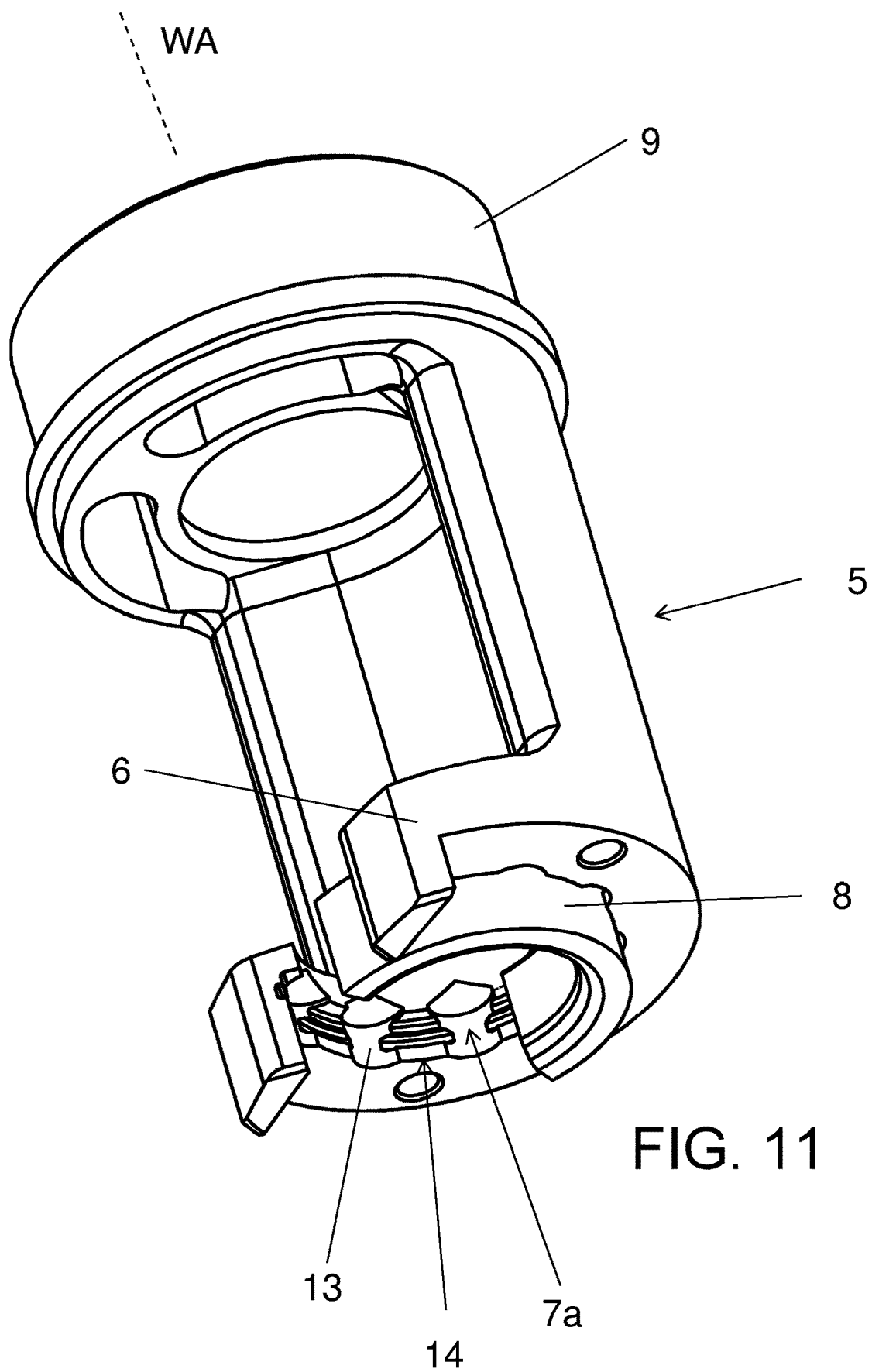

FIG. 11 shows as a further exemplification a closing punch 5, of which the opening 7a, forming the die ring receptacle, is formed at the supporting regions for the die ring 8, in a similar way as with the closing punch 5 in FIG. 10. However, the die ring holder 6 exhibits a reduced height in the direction of the axis WA, such that the die ring 8, also partially represented in FIG. 11, projects over the underside of the die ring holder 6.

Figure 12:
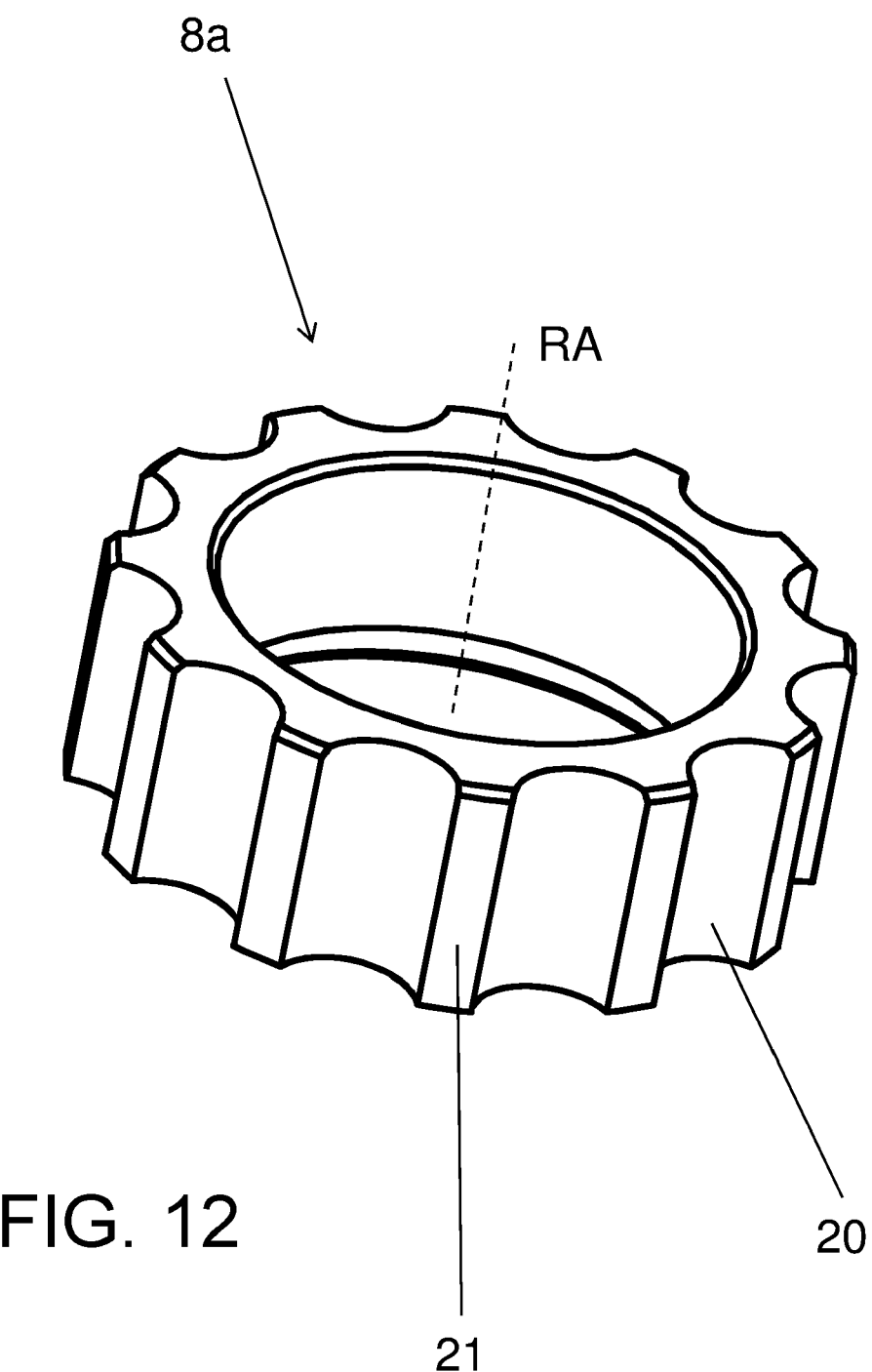
FIGS. 12 and 13, in each case in perspective individual representation, show a die ring for use with the die tool from FIGS. 1.

It has been described heretofore that, in order to form flow channels in the gap 12 between the die ring holder 6 and the die ring 8, the die ring holder 6 is profiled at the contact regions 7.1 and 7.2. Instead of this, or in addition to this, it is also possible for the die ring 8 to be profiled at its circumferential region and/or on its face surface 8.1. FIG. 12 therefore shows, as a further exemplification, a die ring 8a, which is configured at its circumference with a plurality of grooves 20 and intermediate webs 21. The grooves 20 are open to the circumference as well as on the upper side and underside of the die ring 8a. The webs 21 form contact regions or contact surfaces, with which the die ring 8a is radially supported in the opening 7 or 7a, forming the die ring receptacle. The grooves 20 and webs 21 are oriented with their longitudinal extension parallel or essentially parallel to the annular axis RA of the die ring 8a.

Figure 13:
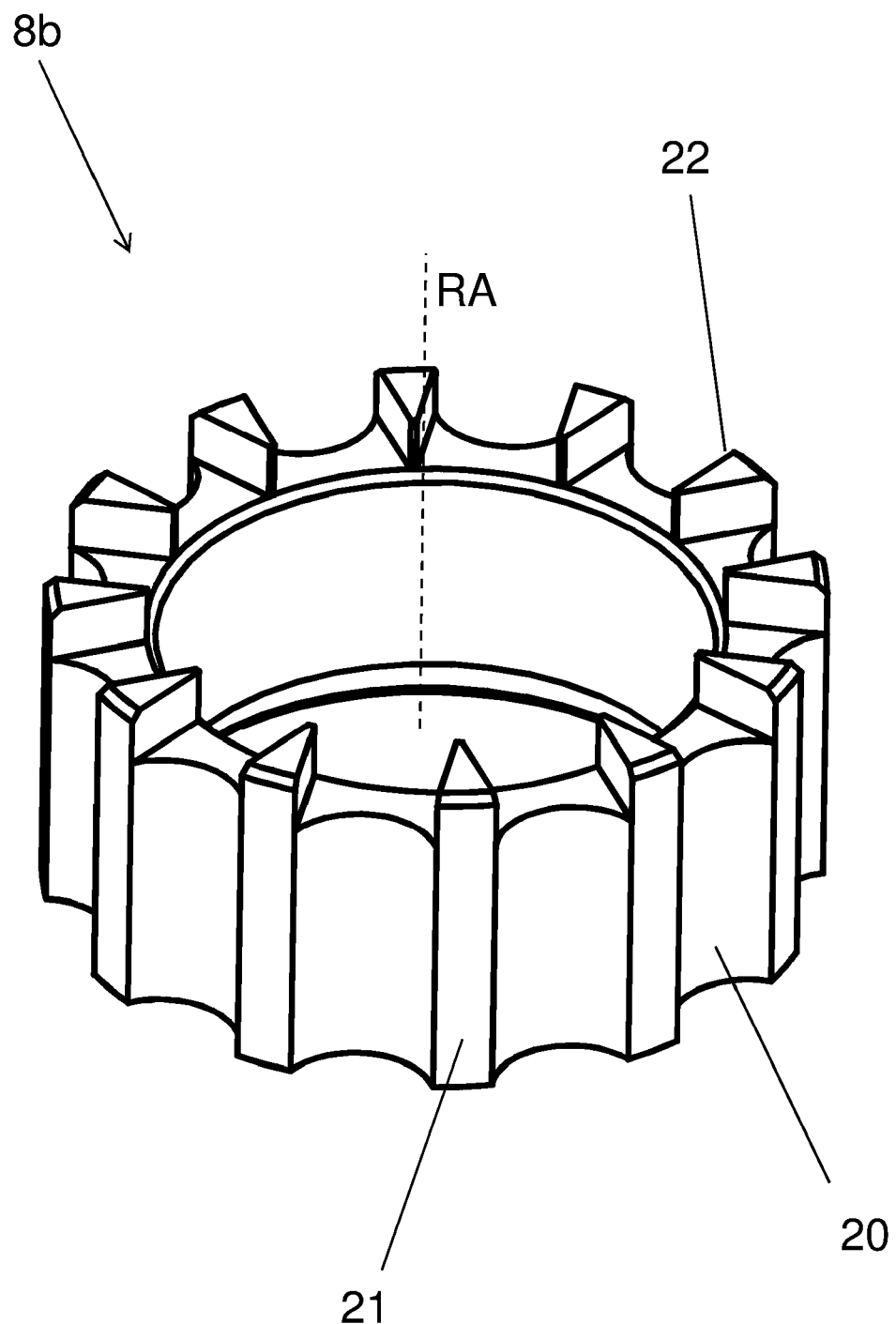

FIG. 13 shows as a further exemplification a die ring 8b, which differs from the die ring 8a in that each web 21 extends on the upper side of the die ring in a projection 22, and there each groove 20 opens into the intermediate space between two projections 22, which in their totality then form the axial contact for the die ring 8b in the opening 7 or 7a respectively, forming the die ring receptacle.

Figure 14:
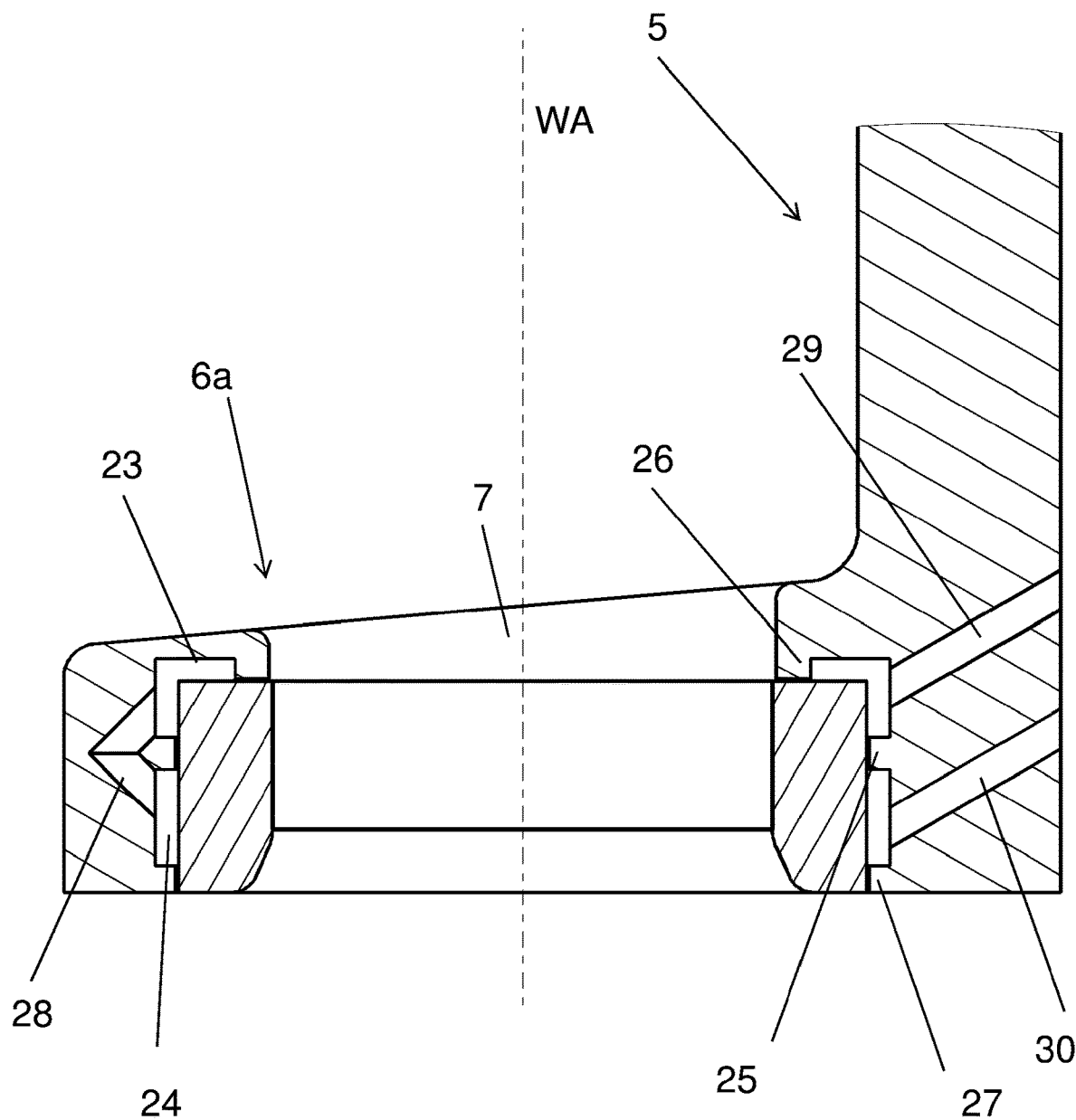
FIG. 14, a representation similar to FIG. 2, shows a further exemplification of the present application.

FIG. 14 shows, in an enlarged individual representation, the die ring holder 6a formed at the lower end of the closing punch 5, in a further exemplification of the closing tool according to the present application. The die ring holder 6a is in turn provided with the opening 7, arranged and formed coaxially with the axis WA, which forms the receptacle for the die ring 8, and which in turn exhibits a reduced cross-section in its upper region or, respectively on the upper side of the die ring holder 6a, in order to form a step which serves as the axial support for the die ring 8.

Formed in the opening 7 are two grooves 23 and 24, surrounding the tool axis WA in annular fashion, which in each case are open towards the opening 7. The groove 23 is formed at the step serving as the axial support of the die ring 8, and on the inner surface of the opening 7, surrounding the die ring 8, while the groove 24 is arranged exclusively on the inner surface of the opening 7, surrounding the die ring. The two grooves 23 and 24 are offset axially to one another, relative to the tool axis WA, and, at least along the greater part of the circumference of the die ring 8, are separated by an annular web 25 surrounding the tool axis WA. On the edges remote from the web 25, the grooves 23 and 24 are in each case delimited by a further annular web 26 (groove 23) and 27 (groove 24) respectively, surrounding in annular fashion the tool axis WA. In this situation, the web 26 forms the axial supporting region for the die ring 8, and the webs 25 and 27 form the radial supporting regions. By way of a cut-out aperture 28 on the inner surface of the opening 7, the two grooves 23 and 24 can be advantageously connected to each other with regard to flow capability, as a result of which the flushing procedure is improved still further. Additionally, two channels 29 and 30 are provided in the die ring holder 6, of which the channel 29 opens into the groove 23, and the channel 30 opens into the groove 24, and which are open on an outer surface of the die ring holder 6a. The two channels 29 and 30 are in this situation in one possible exemplification provided offset by one hundred eighty degrees in relation to the cut-out aperture 28, relative to the tool axis WA. The two channels 29 and 30 and allow for the delivery and removal of the liquid and/or vaporous and/or gaseous treatment medium (in one possible exemplification cleaning and/or sterilization medium) so as to flow through the grooves 23 and 24, and thereby also the gap formed between the die ring holder 6a and the die ring 8, wherein the treatment medium also passes into the gap between the die ring 8 and the webs 25, 26 and 27.

The present application has been described heretofore by way of exemplifications. It is understood that numerous modifications and derivations are possible, without thereby departing from the concept on which the present application is based. By way of example, it has been described heretofore that the grooves 13 and 20 extend parallel or substantially parallel to the axes WA or RA. Another orientation of the grooves is also possible, for example obliquely or in helical fashion to the axis WA or RA. A straight line arrangement of the grooves may also not be absolutely necessary and/or desired. Moreover, it is also possible for the die ring 8, 8a, or 8b to be arranged as floating, i.e. with a certain amount of axial and/or radial play in the opening 7 or 7a respectively of the die ring holder 6.

The present application relates to a closing tool for closing bottles 2 with crown caps 3 or closures of this type by means of a die ring 8 which can be lowered from and returned into a starting position and can be accommodated in a die ring receptacle or opening 7 of a die ring holder 6, said die ring supporting itself on supporting regions formed in the opening in a radial and axial manner relative to the tool axis.

One feature or aspect of an exemplification is believed at the time of the filing of this patent application to possibly reside broadly in a closing tool for closing bottles 2 with crown caps 3 or closures of this type, by means of a die ring 8, 8a, 8b, which can be lowered out of a starting position and returned to this starting position and is accommodated in a die ring receptacle or opening 7, 7a of a die ring holder 6, 6a, which is supported on supporting regions 7.1, 7.2, formed in the die ring receptacle or opening 7, 7a, radially and axially relative to tool axis WA, wherein formed in the gap 12 between the die ring receptacle or opening 7, 7a and adjacent surfaces of the die ring 8, 8a, 8b is at least one flow path through which a liquid and/or vaporous and/or gaseous treatment medium can flow.

Another feature or aspect of an exemplification is believed at the time of the filing of this patent application to possibly reside broadly in the closing tool, wherein, formed in the gap 12 between the die ring receptacle or opening 7, 7a and adjacent surfaces of the die ring 8, 8a, 8b, are a plurality of flow paths, through which a liquid and/or vaporous and/or gaseous treatment medium can flow.

Yet another feature or aspect of an exemplification is believed at the time of the filing of this patent application to possibly reside broadly in the closing tool, wherein the at least one flow path or flow paths are in each case configured as continuous or substantially continuous between an underside and an upper side of the die ring holder 6, 6a and the die ring 8, 8a, 8b, and, related for example to the tool axis WA, extend at least axially or essentially axially, in one possible exemplification also radially or essentially radially, and/or tangentially or essentially tangentially.

Still another feature or aspect of an exemplification is believed at the time of the filing of this patent application to possibly reside broadly in the closing tool, wherein the die ring receptacle or the opening 7, 7a forming this are profiled on their inner surface and/or the die ring 8, 8, 8b is profiled on the circumferential surface and/or face surface supporting the die ring holder 6, 6a, and possibly in each case for the formation of a plurality of raised regions and indentations or troughs, adjacent to these raised regions, and, for example, at least partially surrounding them, and that the raised regions in their totality form the contact surface of the die ring receptacle and/or the contact surface of the die ring 8, 8a, 8b.

Yet another feature or aspect of an exemplification is believed at the time of the filing of this patent application to possibly reside broadly in the closing tool, wherein the surface dimension of the totality of the contact or support surfaces for the die ring 8, 8a, 8b, formed from the raised regions, is perceptibly smaller than the surface dimension which non-profiled contact or support surfaces for the die ring 8, 8a, 8b would comprise in totality, for example by at least fifty percent.

A further feature or aspect of an exemplification is believed at the time of the filing of this patent application to possibly reside broadly in the closing tool, wherein the profiling is configured in the form of grooves 13, 16 and webs 14, 17, 21 lying between them, forming the contact or support surfaces.

Another feature or aspect of an exemplification is believed at the time of the filing of this patent application to possibly reside broadly in the closing tool, wherein the profiling is configured for the support of the die ring 8, 8a, 8b, axially relative to the tool axis WA, by a plurality of projections 15, 22, which are spaced at a distance from one another and are provided distributed about the tool axis WA or the axis RA of the die ring 8b or the opening 7, 7a and/or on a face surface of the die ring 8b.

Yet another feature or aspect of an exemplification is believed at the time of the filing of this patent application to possibly reside broadly in the closing tool, wherein the grooves 13, 20 forming the profiling are configured with their longitudinal extension parallel or essentially parallel to the tool axis WA or to an axis RA of the die ring 8a, 8b or obliquely or in helical form relative to these axes WA, RA.

Still another feature or aspect of an exemplification is believed at the time of the filing of this patent application to possibly reside broadly in the closing tool, wherein indentations or additional grooves 16 are provided in the webs 14, which in each case open at both ends into a groove 13 separating two webs 14, and are oriented, for example relative to the machine axis WA or relative to the axis RA of the die ring 8, 8a, 8b, tangentially or essentially tangentially. A further feature or aspect of an exemplification is believed at the time of the filing of this patent application to possibly reside broadly in the closing tool, wherein the projections 15 serving to provide the axial support for the die ring 8, 8a, 8b are formed in each case at a web 14, and in one possible exemplification transfer into a common projection 18, which is formed annular in shape, and, surrounding the tool axis WA, extends into the die ring receptacle or into the opening 7a forming this receptacle.

Another feature or aspect of an exemplification is believed at the time of the filing of this patent application to possibly reside broadly in the closing tool, wherein in the die ring holder 6a at least one channel 29, 30 is provided, opening into the gap between the die ring holder 6a and adjacent surfaces of the die ring 8, 8a, 8b, for delivering and removing the treatment medium, wherein the at least one channel 29, 30 is open, in one possible exemplification on a surface of the die ring holder 6a outside the die ring receptacle or the opening 7, 7a forming this receptacle.

Yet another feature or aspect of an exemplification is believed at the time of the filing of this patent application to possibly reside broadly in the closing tool, wherein in the at least one channel 29, 30 opens into at least one groove 23, 24, formed in the die ring receptacle or opening 7, and surrounding the tool axis WA, for example at least partially, wherein, for example, two grooves 23, 24, offset axially to one another relative to the tool axis WA, are provided, into which in each case at least one channel 29, 30 opens, and which are in one possible exemplification connected to one another with regard to flow movement.

Still another feature or aspect of an exemplification is believed at the time of the filing of this patent application to possibly reside broadly in the closing tool, wherein in the webs 25, 26, 27, delimiting the at least one groove 23, 24 laterally, form the axial and radial supporting regions of the die ring, and that this supporting region in one possible exemplification comprises the profiling.

One feature or aspect of an exemplification is believed at the time of the filing of this patent application to possibly reside broadly in a die ring for use with a closing tool according to the present application, wherein the closing ring 8a, 8b comprises the profiling at its circumferential surface or casing surface and/or on at least one face surface.

One feature or aspect of an exemplification is believed at the time of the filing of this patent application to possibly reside broadly in a bottle closing device for pressing press-fit closures, such as crown corks, crown caps, and similar closures, on bottles, said bottle closing device comprising: a support portion and a head portion connected to an end of said support portion to engage a press-fit closure; said head portion comprising a support body and a die ring disposed in an opening in said support body; said support portion being movable to press said die ring against a press-fit closure and deform a portion of a press-fit closure to secure a press-fit closure to a bottle; and said die ring and said support body together form at least one flow passage, which said at least one flow passage, upon treatment of said head portion, permits flow of liquid and/or vaporous and/or gaseous treatment medium between said die ring and said support body.

Another feature or aspect of an exemplification is believed at the time of the filing of this patent application to possibly reside broadly in the bottle closing device, wherein said at least one flow passage comprises a plurality of flow passages.

Yet another feature or aspect of an exemplification is believed at the time of the filing of this patent application to possibly reside broadly in the bottle closing device, wherein: said support portion is configured to be moved back and forth along its longitudinal axis; said flow passages run continuously between a first end and a second end of said support body; and said flow passages extend, with respect to said longitudinal axis, axially or essentially axially, and/or radially or essentially radially, and/or tangentially or essentially tangentially.

Still another feature or aspect of an exemplification is believed at the time of the filing of this patent application to possibly reside broadly in the bottle closing device, wherein: said die ring comprises first and second end faces and a side surface disposed between and transverse to said first and second end faces; said support body comprises an inner surface disposed about said opening therein and to face said side surface of said die ring; said inner surface of said support body comprises raised surface sections and lowered surface sections; said lowered surface sections form said flow passages; and said raised surface sections together form a contact surface to contact said die ring.

A further feature or aspect of an exemplification is believed at the time of the filing of this patent application to possibly reside broadly in the bottle closing device, wherein the total surface area of said raised surface sections is substantially less than the total surface area of said inner surface.

Another feature or aspect of an exemplification is believed at the time of the filing of this patent application to possibly reside broadly in the bottle closing device, wherein: said support body comprises a plurality of alternating grooves and webs; said lowered surface sections are disposed on said grooves; and said raised surface sections are disposed on said webs.

Yet another feature or aspect of an exemplification is believed at the time of the filing of this patent application to possibly reside broadly in the bottle closing device, wherein: each of said webs projects inwardly a distance sufficient to contact and support said side surface of said die ring; each of said webs comprises a projecting portion disposed adjacent said first end of said support body; and said projecting portions project inwardly beyond said side surface of said die ring to contact and support said first end face of said die ring.

Still another feature or aspect of an exemplification is believed at the time of the filing of this patent application to possibly reside broadly in the bottle closing device, wherein said grooves are elongated and disposed to extend parallel or essentially parallel or obliquely or helically relative to the longitudinal axis or to a central axis of said die ring.

A further feature or aspect of an exemplification is believed at the time of the filing of this patent application to possibly reside broadly in the bottle closing device, wherein: each of said webs comprises additional grooves formed therein; and each of said additional grooves extends across its web between the two grooves on either side of its web tangentially or essentially tangentially relative to said longitudinal axis of said support portion or said central axis of said die ring.

Another feature or aspect of an exemplification is believed at the time of the filing of this patent application to possibly reside broadly in the bottle closing device, wherein said projecting portions of said webs are joined by or to form a common annular projection disposed about said longitudinal axis.

Yet another feature or aspect of an exemplification is believed at the time of the filing of this patent application to possibly reside broadly in the bottle closing device, wherein: said support body comprises at least one channel disposed to run through said support body; and said at least one channel comprises a first opening disposed in one of said lowered surface sections, and a second opening disposed on an outer surface of said support body, to permit delivery and removal of treatment medium to and from said passages.

Still another feature or aspect of an exemplification is believed at the time of the filing of this patent application to possibly reside broadly in the bottle closing device, wherein: said at least one flow passage comprises a first annular groove and a second annular groove formed in said support body and disposed about said die ring; said support body comprises an annular projection disposed to separate said first and second annular grooves; said support body comprises an inlet channel and an outlet channel disposed to run through said support body; said inlet channel comprises a first opening disposed to open into said first annular groove, and a second opening disposed on an outer surface of said support body, to permit delivery of treatment medium into said first annular groove; said outlet channel comprises a first opening disposed to open into said second annular groove, and a second opening disposed on an outer surface of said support body, to permit removal of treatment medium from said second annular groove; said support body comprises at least one connecting channel disposed to run through said support body; and said at least one connecting channel comprises a first opening disposed to open into said first annular groove, and a second opening disposed to open into said second annular groove, to permit circulating flow of treatment medium into and out of said first and second annular grooves.

A further feature or aspect of an exemplification is believed at the time of the filing of this patent application to possibly reside broadly in the bottle closing device, wherein: said die ring comprises first and second end faces and a side surface disposed between and transverse to said first and second end faces; said support body comprises an inner surface disposed about said opening therein and to face said side surface of said die ring; said side surface of said die ring comprises raised surface sections and lowered surface sections; said lowered surface sections form said flow passages; and said raised surface sections together form a contact surface to contact said support body.

Another feature or aspect of an exemplification is believed at the time of the filing of this patent application to possibly reside broadly in the bottle closing device, wherein the total surface area of said raised surface sections is substantially less than the total surface area of said side surface.

Yet another feature or aspect of an exemplification is believed at the time of the filing of this patent application to possibly reside broadly in the bottle closing device, wherein: said die ring comprises a plurality of alternating grooves and webs; said lowered surface sections are disposed on said grooves; and said raised surface sections are disposed on said webs.

Still another feature or aspect of an exemplification is believed at the time of the filing of this patent application to possibly reside broadly in the bottle closing device, wherein: each of said webs comprises a projecting portion disposed to project from said first end face of said die ring; and said projecting portions are spaced apart and disposed to project toward and contact a portion of said support body.

A further feature or aspect of an exemplification is believed at the time of the filing of this patent application to possibly reside broadly in the bottle closing device, wherein said at least one flow passage is configured to permit flow of liquid and/or vaporous and/or gaseous cleaning and/or disinfecting medium between said die ring and said support body to permit cleaning and/or disinfecting of surfaces of said die ring and said support body.

Another feature or aspect of an exemplification is believed at the time of the filing of this patent application to possibly reside broadly in a method of treating the bottle closing device, the method comprising flowing liquid and/or vaporous and/or gaseous cleaning and/or disinfecting medium into said at least one flow passage between said die ring and said support body, and thereby cleaning and/or disinfecting surfaces of said die ring and said support body.

One feature or aspect of an exemplification is believed at the time of the filing of this patent application to possibly reside broadly in a die ring installable in a bottle closing device for pressing press-fit closures, such as crown corks, crown caps, and similar closures, on bottles, which bottle closing device comprises a support body to hold and support said die ring, said die ring comprising: first and second end faces and a side surface disposed between and transverse to said first and second end faces; said side surface comprising raised surface sections and lowered surface sections; said raised surface sections together form a contact surface, which contact surface, upon installation of said die ring in a support body of a bottle closing device, contacts a surface of the support body; and said lowered surface sections form flow passages, which flow passages, upon installation of said die ring in a support body of a bottle closing device, permit flow of liquid and/or vaporous and/or gaseous treatment medium between said die ring and a support body of a bottle closing device upon treatment of a bottle closing device with a treatment medium.

Another feature or aspect of an exemplification is believed at the time of the filing of this patent application to possibly reside broadly in the die ring installable in a bottle closing device, wherein: said die ring comprises a plurality of alternating grooves and webs; said lowered surface sections are disposed on said grooves; said raised surface sections are disposed on said webs; each of said webs comprises a projecting portion disposed to project from said first end face of said die ring; said projecting portions are spaced apart; said projecting portions, upon installation of said die ring in a support body of a bottle closing device, project toward and contact a portion of the support body.

The components disclosed in the patents, patent applications, patent publications, and other documents disclosed or incorporated by reference herein, may possibly be used in possible exemplifications of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one exemplification of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various exemplifications may be used with at least one exemplification or all of the exemplifications, if more than one exemplification is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications, patent publications, and other documents cited herein, and in the Declaration attached hereto, are hereby incorporated by reference as if set forth in their entirety herein except for the exceptions indicated herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, patent applications, patent publications, and other documents which are included in this application and which are referred to in paragraphs which state "Some examples of . . . which may possibly be used in at least one possible exemplification of the present application . . . " may possibly not be used or useable in any one or more exemplifications of the application.

The sentence immediately above relates to patents, patent applications, patent publications, and other documents either incorporated by reference or not incorporated by reference.

The following patents, patent applications, patent publications, and other documents, except for the exceptions indicated herein, are hereby incorporated by reference as if set forth in their entirety herein except for the exceptions indicated herein, as follows: DE 39 18 504, having the title "VERSCHLIESSMASCHINE UMLAUFENDER BAUART", published on Dec. 13, 1990.

All of the patents, patent applications, patent publications, and other documents, except for the exceptions indicated herein, which were cited in the German Office Action dated Jul. 21, 2015, and/or cited elsewhere, as well as the German Office Action document itself, are hereby incorporated by reference as if set forth in their entirety herein except for the exceptions indicated herein, as follows: DE 196 26 680 A1, having the title "Closing element for bottle closing machine using crown corks", published on Jan. 8, 1998; and DE 43 32 740, having the title "Sealing element", published on Mar. 30, 1995.

All of the patents, patent applications, patent publications, and other documents, except for the exceptions indicated herein, which were cited in the International Search Report dated Jan. 18, 2016, and/or cited elsewhere, as well as the International Search Report document itself, are hereby incorporated by reference as if set forth in their entirety herein except for the exceptions indicated herein, as follows: GB 770 745 A, having the title "Improvements in or relating to apparatus for closing bottles by means of crown corks", published on Mar. 20, 1957; and DE 41 10 456 A1, having the title "Crown cork closing head—has device which flushes cleaning fluid through its interior", published on Mar. 19, 1992.

The corresponding foreign and international patent publication applications, namely, Federal Republic of Germany Patent Application No. 10 2014 114 561.5, filed on Oct. 7, 2014, having inventor Matthias NAABER, and DE-OS 10 2014 114 561.5 and DE-PS 10 2014 114 561.5, and International Application No. PCT/EP2015/072527, filed on Sep. 30, 2015, having WIPO Publication No. WO 2016/055323 and inventor Matthias NAABER, are hereby incorporated by reference as if set forth in their entirety herein, except for the exceptions indicated herein, for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications, patent publications, and other documents, except for the exceptions indicated herein, are hereby incorporated by reference as if set forth in their entirety herein except for the exceptions indicated herein.

The purpose of incorporating the corresponding foreign equivalent patent application(s), that is, PCT/EP2015/072527 and German Patent Application 10 2014 114 561.5, is solely for the purposes of providing a basis of correction of any wording in the pages of the present application, which may have been mistranslated or misinterpreted by the translator, and to provide additional information relating to technical features of one or more exemplifications, which information may not be completely disclosed in the wording in the pages of this application.

Statements made in the original foreign patent applications PCT/EP2015/072527 and DE 10 2014 114 561.5 from which this patent application claims priority which do not have to do with the correction of the translation in this patent application are not to be included in this patent application in the incorporation by reference.

Any statements about admissions of prior art in the original foreign patent applications PCT/EP2015/072527 and DE 10 2014 114 561.5 are not to be included in this patent application in the incorporation by reference, since the laws relating to prior art in non-U.S. Patent Offices and courts may be substantially different from the Patent Laws of the United States.

Some example of cleaning systems or CIP cleaning systems and/or components thereof, which may possibly be utilized or adapted for use in at least one possible exemplification, may possibly be found in the following U.S. Pat. Nos. 9,522,818; 9,475,681; 9,340,402; 9,242,280; 8,776,842; 8,459,315; 8,006,464; 7,104,033; and 6,918,417.

All of the references and documents cited in any of the patents, patent applications, patent publications, and other documents cited herein, except for the exceptions indicated herein, are hereby incorporated by reference as if set forth in their entirety herein except for the exceptions indicated herein. All of the patents, patent applications, patent publications, and other documents cited herein, referred to in the immediately preceding sentence, include all of the patents, patent applications, patent publications, and other documents cited anywhere in the present application.

Words relating to the opinions and judgments of the author of all patents, patent applications, patent publications, and other documents cited herein and not directly relating to the technical details of the description of the exemplifications therein are not incorporated by reference.

The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the abovementioned words in this sentence, when not used to describe technical features of one or more exemplifications of the patents, patent applications, patent publications, and other documents, are not considered to be incorporated by reference herein for any of the patents, patent applications, patent publications, and other documents cited herein.

The description of the exemplification or exemplifications is believed, at the time of the filing of this patent application, to adequately describe the exemplification or exemplifications of this patent application. However, portions of the description of the exemplification or exemplifications may not be completely applicable to the claims as originally filed in this patent application, as amended during prosecution of this patent application, and as ultimately allowed in any patent issuing from this patent application. Therefore, any statements made relating to the exemplification or exemplifications are not intended to limit the claims in any manner and should not be interpreted as limiting the claims in any manner.

The details in the patents, patent applications, patent publications, and other documents cited herein may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the exemplification or exemplifications, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. § 1.72(b). As stated in 37 C.F.R. § 1.72(b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The exemplifications of the invention described herein above in the context of the preferred exemplifications are not to be taken as limiting the exemplifications of the invention to all of the provided details thereof, since modifications and variations thereof may be made without departing from the spirit and scope of the exemplifications of the invention.

AT LEAST PARTIAL NOMENCLATURE

1 Closing tool
2 Bottle
3 Crown caps
4 Hold-down element
4.1 Hold-down spring
5 Closing punch
6, 6a Die ring holder
7, 7a Opening
7.1, 7.2 Supporting region
8, 8a, 8b Die ring
8.1 Die ring edge
9 Connecting or holding section
10 Housing part
11 Plate
12 Gap
13 Groove
13.1 Opening 14 Web
15 Projection
16 Groove
17 Web
18 Projection
19 Flow channel
20 Groove
21 Web
22 Projection
23, 24 Groove
25, 26, 27 Web
28 Cut-out aperture
29, 30 Channel
A Movement of the closing punch 5
B Flow through the gap 12
RA Ring axis
WA Axis of the closing tool 1

What is claimed is:

1. A bottle closing device configured to close bottle mouths with press-fit closures, such as crown corks, or crown caps, and similar closures, or caps, said bottle closing device comprising:
a support portion and a head portion connected to an end of said support portion;
said head portion comprising a support body and a die ring disposed in an opening in said support body;
said support portion being movable to press said die ring against, and thereby deform, a press-fit closure, a crown cork, or a crown cap onto a mouth portion of a bottle;
said die ring comprises first and second end faces and a side surface disposed between and transverse to said first and second end faces;
said support body comprises an inner surface disposed about said opening therein and to face said side surface of said die ring;
said die ring and said support body together form at least one flow passage, which said at least one flow passage, upon treatment of said head portion, permits flow of liquid and/or vaporous and/or gaseous treatment medium between said die ring and said support body; and
wherein each said at least one flow passage has a radial flow portion between said first end face of said die ring and said support body and an axial flow portion extending between said inner surface of said support body and said side surface of said die ring.

2. The bottle closing device according to claim 1, wherein said at least one flow passage comprises a plurality of flow passages.

3. The bottle closing device according to claim 2, wherein:
said support portion is configured to be moved back and forth along its longitudinal axis;
said flow passages run continuously between a first end and a second end of said support body; and
said flow passages extend, with respect to said longitudinal axis, axially or essentially axially.

4. The bottle closing device according to claim 3, wherein:
said die ring comprises first and second end faces and a side surface disposed between and transverse to said first and second end faces;
said support body comprises an inner surface disposed about said opening therein and to face said side surface of said die ring;
said inner surface of said support body comprises raised surface sections and lowered surface sections;
said lowered surface sections form said flow passages; and
said raised surface sections together form a contact surface to contact said die ring.

5. The bottle closing device according to claim 4, wherein the total surface area of said raised surface sections is substantially less than the total surface area of said inner surface.

6. The bottle closing device according to claim 5, wherein:
said support body comprises a plurality of alternating grooves and webs;
said lowered surface sections are disposed on said grooves; and
said raised surface sections are disposed on said webs.

7. The bottle closing device according to claim 6, wherein:
each of said webs projects inwardly a distance sufficient to contact and support said side surface of said die ring;
each of said webs comprises a projecting portion disposed adjacent said first end of said support body; and
said projecting portions project inwardly beyond said side surface of said die ring to contact and support said first end face of said die ring.

8. The bottle closing device according to claim 7, wherein said grooves are elongated and disposed to extend parallel or essentially parallel or obliquely or helically relative to the longitudinal axis or to a central axis of said die ring.

9. The bottle closing device according to claim 2, wherein each of said flow passages comprises:
a first section disposed to extend, with respect to said longitudinal axis, radially or essentially radially; and
a second section disposed to extend, with respect to said longitudinal axis, axially or essentially axially.

10. The bottle closing device according to claim 9, wherein:
said support body comprises an inner shoulder surface disposed to face said first end face of said die ring;
said first section of each of said flow passages is formed in said inner shoulder surface of said support body; and
said second section of each of said flow passages is formed in said inner surface of said support body.

11. The bottle closing device according to claim 1, wherein said at least one flow passage is configured to permit flow of liquid and/or vaporous and/or gaseous cleaning and/or disinfecting medium between said die ring and said support body to permit cleaning and/or disinfecting of surfaces of said die ring and said support body.

12. The bottle closing device according to claim 1, wherein said at least one flow passage comprises:
a first section disposed to extend, with respect to said longitudinal axis, radially or essentially radially; and
a second section disposed to extend, with respect to said longitudinal axis, axially or essentially axially.

13. The bottle closing device according to claim 12, wherein:
said support body comprises an inner shoulder surface disposed to face said first end face of said die ring;
said first section of said at least one flow passage is formed in said inner shoulder surface of said support body; and
said second section of said at least one flow passage is formed in said inner surface of said support body.

14. A method of treating a bottle closing device according to claim 11, said method comprising flowing liquid and/or vaporous and/or gaseous cleaning and/or disinfecting medium into said at least one flow passage between said die ring and said support body, and thereby cleaning and/or disinfecting surfaces of said die ring and said support body.

* * * * *